United States Patent

Wang

Patent Number: 5,385,060
Date of Patent: Jan. 31, 1995

[54] DEVICE FOR THE ASSEMBLY OR DISASSEMBLY OF PROBES IN PROCESS PIPES, TANKS, ETC.

[76] Inventor: Kjetil Wang, Wessels gt. 19, N-7043 Trondheim, Norway

[21] Appl. No.: 910,028
[22] PCT Filed: Dec. 3, 1991
[86] PCT No.: PCT/NO91/00150
 § 371 Date: Mar. 22, 1993
 § 102(e) Date: Mar. 22, 1993
[87] PCT Pub. No.: WO92/09723
 PCT Pub. Date: Jun. 11, 1992

[30] Foreign Application Priority Data

Dec. 3, 1990 [NO] Norway ................................ 905216

[51] Int. Cl.6 ....................... G01M 19/00; B23P 19/04
[52] U.S. Cl. ........................................... 73/866.5; 73/86;
 29/700; 29/705; 29/252; 137/323; 137/328;
 137/559
[58] Field of Search ................. 73/866.5, 86; 374/148,
 374/208; 422/53; 137/315, 316, 320–323, 327,
 328, 559; 29/407, 426.1–426.6, 428, 700, 705,
 221.6, 252

[56] References Cited

U.S. PATENT DOCUMENTS

| | | | |
|---|---|---|---|
| 3,174,332 | 3/1965 | Echtler et al. | 73/86 |
| 3,718,034 | 2/1973 | Swearingen | 73/86 |
| 4,026,001 | 5/1977 | Jones | 29/426.5 |
| 4,096,754 | 6/1978 | Beveridge, Jr. et al. | 73/866.5 |
| 4,177,676 | 12/1979 | Welker | 73/866.5 X |
| 4,916,797 | 4/1990 | Strömmen et al. | 29/426.5 |

FOREIGN PATENT DOCUMENTS

| | | | |
|---|---|---|---|
| 139281 | 1/1979 | Denmark . | |
| 8041 | 2/1980 | European Pat. Off. . | |
| 105212 | 5/1991 | Japan | 73/866.5 |
| 162832 | 11/1989 | Norway . | |
| 2096929 | 10/1982 | United Kingdom | 29/221.6 |

*Primary Examiner*—Tom Noland
*Attorney, Agent, or Firm*—James E. Pittenger

[57] ABSTRACT

A retrieving device for the assembly and disassembly of probes into process pipes and tanks comprising a hydraulically activated cylinder attached to a nipple and ball valve mounted on the wall of a pipe or tank and the cylinder may be operated by applying a suitable pump. A pair of pistons are inserted within the cylinder and these pistons are arranged in telescoping fashion. A piston rod attached to one of the pistons is constructed so that it can securely attach to a probe or other device. a fluid pressurizing means which includes a pair of hydraulic tubes are attached to the upper and lower ends of the hydraulic cylinder so that hydraulic pressure can be applied to extend the pistons and insert the probe or retract the pistons and remove the probe. The ball valve is closed and the retrieving device can then be removed from the valve to service and replace the probe. When the probe is inserted within the nipple a sealing device seals the probe against fluid leakage from the pipe or tank. The probe is then held in position within the nipple by a plurality of set screws or plugs.

5 Claims, 4 Drawing Sheets

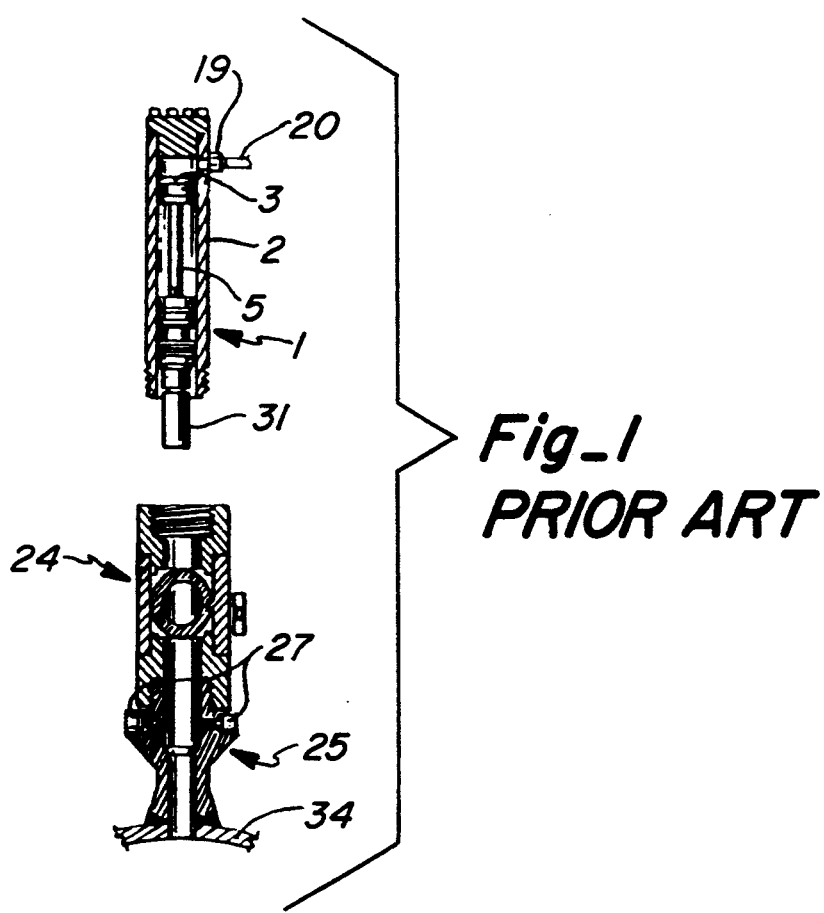
Fig_1
PRIOR ART
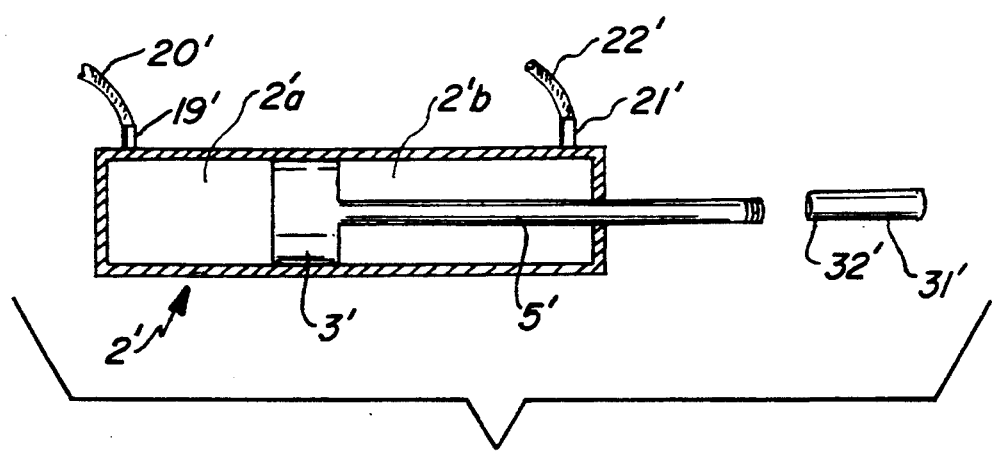
Fig_2
PRIOR ART

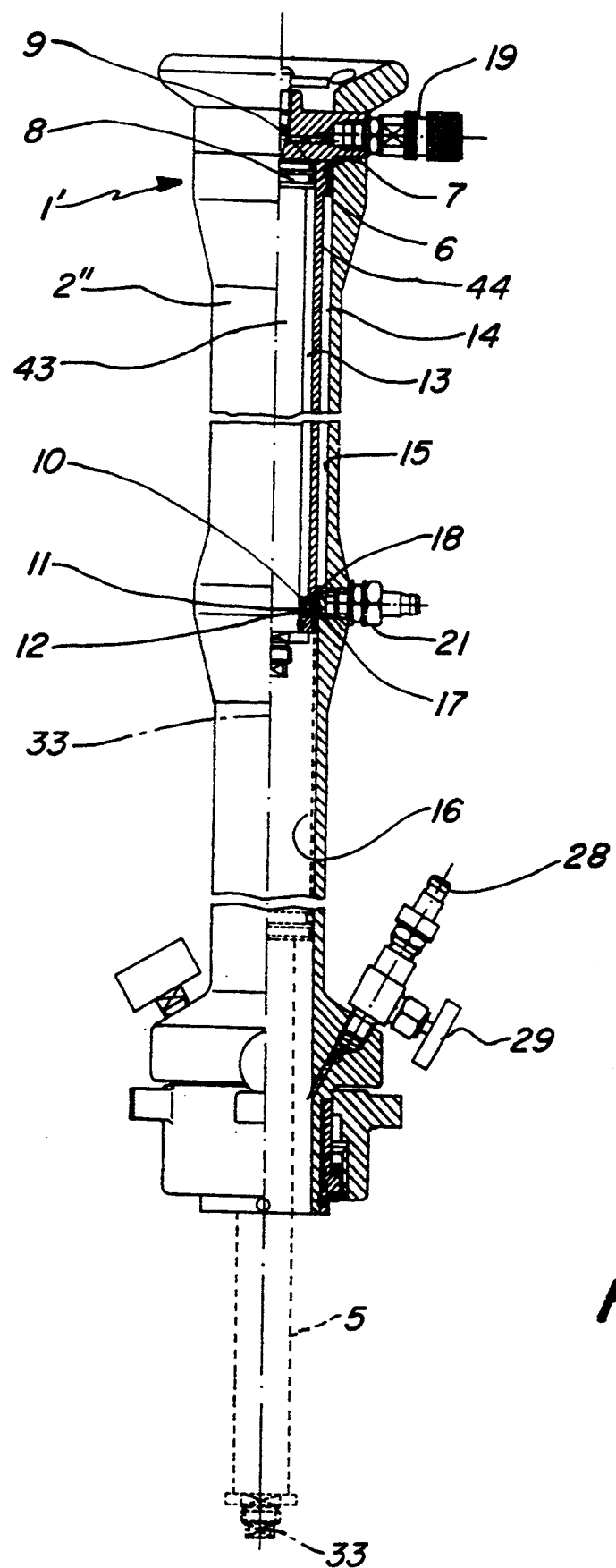
Fig_3

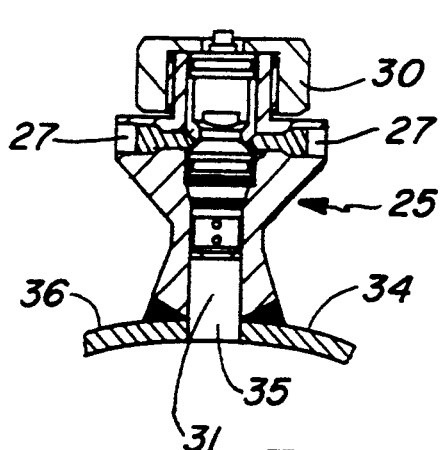
Fig_4
PRIOR ART
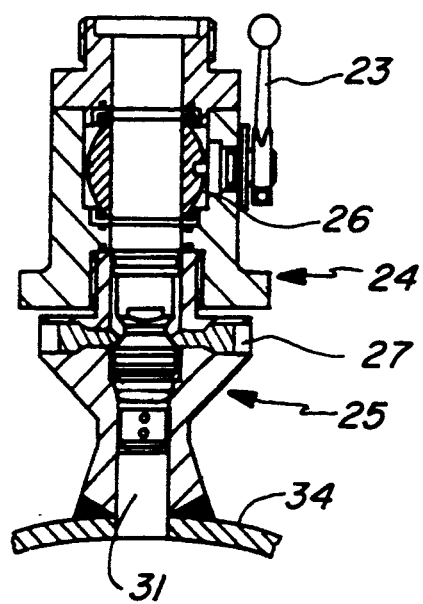
Fig_5
PRIOR ART
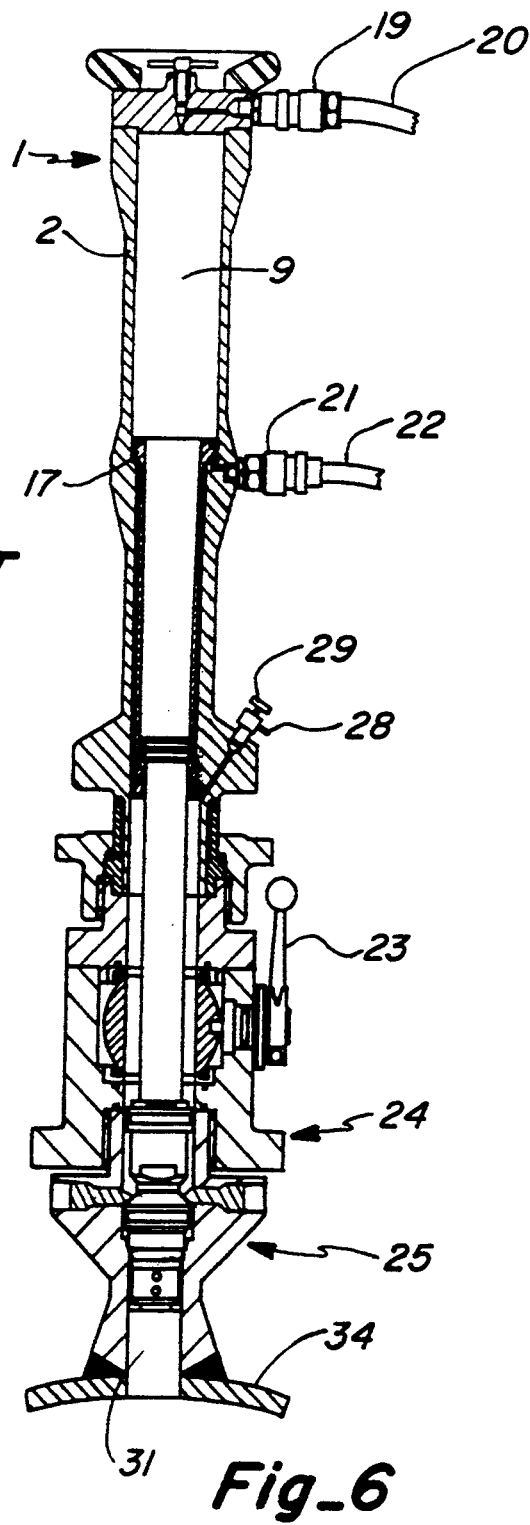
Fig_6

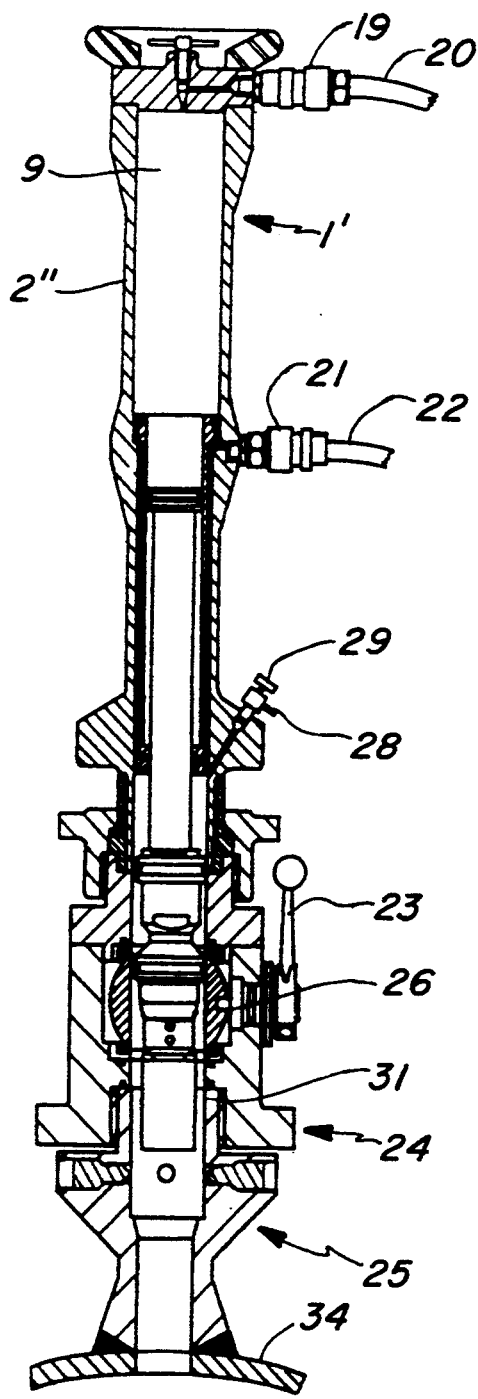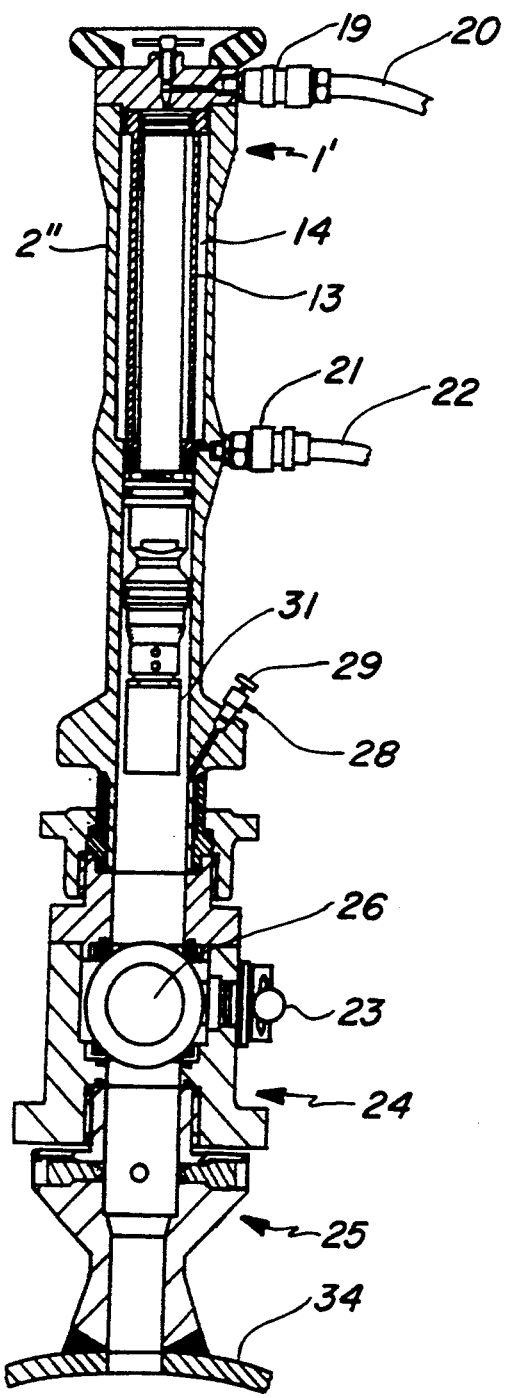
Fig_7   Fig_8

DEVICE FOR THE ASSEMBLY OR DISASSEMBLY OF PROBES IN PROCESS PIPES, TANKS, ETC.

FIELD OF THE INVENTION

The present invention concerns a device for the assembly and disassembly of probes in process pipes, tanks, etc.

BACKGROUND OF THE INVENTION

Probes and similar devices are often employed, especially within the oil, gas and process industry, among other things in order to monitor any corrosion in the internal system. For example, this may be corrosion probes or weightloss coupons which are screwed into process tubing, into well heads, into water injection systems, etc. By using a small threaded nipple or recess fitting with internal threads and a sealing system, a probe may be positioned within the pipe, putting it in direct contact with the process medium.

When it comes to corrosion of probes as well as weightloss coupons, these items must be replaced relatively often. This may, for example, be due to the variable and short working life of probes and planned inspections in connection with weightloss coupons.

In order to carry out such replacements, the traditional method has been the application of mechanical tools, such as so-called retrievers. This involves a ball valve which may be threaded directly onto the nipple into which the probe is threaded. Further, a mechanical retriever is connected, which comprises a double cylinder and an internal, axially movable and rotable rod which makes it possible to move a threaded plug with a probe into or out of the nipple.

A significant disadvantage with the traditional mechanical system is that the cylinder with the rod is very long, ordinarily between 1.8 and 2.0 meters. This sets significant limitations on practical usage, insofar as use with nipples which are located near other pipes or close to decks, floors or ceilings. Often these items cannot be serviced due to lack of space. The movable cylinder with the connecting rod can also represent an element of risk, since quick, axial displacement which may occur as the result of lack of pressure blancing in the retriever may cause injury to the operator. The relatively heavy weight of these devices also represents a disadvantage, inasmuch as both transportation as well as operation of the tool is physically difficult.

A device is shown in U.S. Pat. No. 4,916,797 which in a large degree solves the problems connected to known mechanical retrievers. In this publication, a device is shown which does not require the use of an internal rod with the mechanical transfer of the rod in or out of the nipple. Instead, the plug is fastened into the nipple which makes rotation of the device unnecessary. Further, the plug and probe are constructed with sealing rings so that by taking advantage of the hydraulic pressure differences, the probe and plug may be pushed into or out of the nipple.

However, the hydraulic retriever which is disclosed in U.S. Pat. No. 4,916,797 may only be employed upon the availability of excess pressure in the pipe or tank. Further, the probe may jam in some instances, so that the excess pressure in the pipe is not high enough to be able to allow it to be removed. In such cases, mechanical retrievers must be used. Then, the disadvantage arises where one may employ the familiar hydraulic retriever in those cases in which access is difficult, but additionally there must be made available a mechanic retriever for those places where there is a vacuum, low pressure, no pressure difference or a low excess pressure in the pipe or tank.

SUMMARY OF THE INVENTION

The object of the present invention is to provide a device which also may be used in situations where there is insufficient excess pressure to remove a probe.

This object is achieved through use of a device having a cylinder containing a double telescoping piston to minimize the overall length of the cylinder to allow it to be used in locations having minimal clearance.

BRIEF DESCRIPTION OF THE DRAWINGS

The invention will be described more in detail by way of example of construction and with reference to the accompanying drawings, wherein FIG. 1 is a sectional view of a hydraulic retriever according to the prior art, FIG. 2 is a diagrammatic view of a first embodiment of a hydraulic retriever according to the present invention, FIG. 3 is a partial sectional view of a second embodiment of a hydraulic retriever according to the present invention, FIG. 4 is a sectional view of a prior art nipple which can be used with a hydraulic retriever according to the present invention, FIG. 5 is a sectional view of a ball valve for use with a hydraulic retriever according to the present invention, FIG. 6 is a sectional view of a third embodiment of a hydraulic retriever according to the present invention, in a first position, FIG. 7 is a view of the hydraulic retriever of FIG. 6 in a second position, and FIG. 8 is a view of the hydraulic receiver of FIG. 6 in a third position.

DETAILED DESCRIPTION OF THE PREFERRED EMBODIMENT

FIG. 1 shows a hydraulic retriever according to the of prior art. The retriever is generally designated with the reference numeral 1, and includes a cylinder 2 into which is placed a piston 3 with a piston rod 5. In the cylinder 2 is placed an attachment 19 for hydraulic fluid via a pipe 20. The piston rod 5 in the figure is shown mounted to a probe 31, which in this case is pulled out of or placed into a pipe or placed into a pipe or tank 34. Throughout this invention the term probe 31, includes both the sensor component, or other similar device, and organ which is connected to the sensor in order to keep it in place, for example a plug component. A nipple 25 is mounted to the pipe or tank 34. The probe 31 is fastened to the nipple with the help of set screws or plugs 27, for example four spaced around the circumference. A ball valve, generally designated 24, is mounted to the nipple 25. The use of this prior art hydraulic retriever is previously described in U.S. Pat. No. 4,916,797.

FIG. 2 illustrates in principle one embodiment of a hydraulic retriever according to present invention. It comprises a double-acting cylinder, generally designated as 2'. Two compartments, 2'a and 2'b, respectively, are delimited between the cylinder wall and the two sides of the piston 3'. In addition to the attachment 19' and the pipe 20' for supply of hydraulic fluid, there is additional supply 21' with corresponding tube 22' for hydraulic fluid. This double-acting piston functions by letting hydraulic fluid supplied through the attachment 19' flow back through the attachment 21', and vice versa. Now, when a probe 31' is to be inserted into a pipe or tank 34, the piston 3' is put into effect so that the hydraulic fluid may flow through the attachment 19'. The piston is then pressed against the pipe or tank 34. Upon withdrawal from the pipe or tank 34, the cylinder compartment 2'b is activated by the hydraulic fluid passing through the attachment 21', and the hydraulic fluid in the cylinder compartment 2a flows out through the attachment 19'. The piston rod 5' is arranged to be fastened to an attachment 32' on the probe 31'. For example, the attachment 32' may be threaded. The tractive power in the cylinder compartment 2'b affects the probe 31', and it may be withdrawn from the pipe or tank 34 even if there is low pressure, or if the probe 31' has become stuck for other reasons.

FIG. 3 illustrates still another embodiment of a hydraulic retriever 1' according to the present invention. Here, the cylinder has been scaled down by a shoulder 17, to create a first cylinder wall 15 which has a larger inner diameter than a second cylinder wall 16 which is located closer to the probe. Further, the piston 3' is divided into two piston bodies 43 and 44. The first piston 43 is placed inside the other piston 44, which is hollow. The piston 44 is constructed with a protruding part 6 in one end, which is placed against the cylinder wall 15. At the opposite end of the piston 44, a movable sealing component 10 has been inserted, which seals with an O-ring 12 against the piston rod 5, connected to the piston 44. The inwardly protruding component 10 seals against the cylinder wall 16 with an O-ring 11. A cavity 9 is created when the piston's components 43 and 44 move forward, that is when hydraulic fluid flows through the attachment 19. It is this cavity which creates the "pulling inward" movement. The piston 43 has a protruding part 8 which seals against the inner wall of the piston 44. In this manner, a first cavity 13 is created between the first piston 43 and the other piston 44, and a second cavity 14 is created between the second piston 44 and the cylinder wall 15. In the piston 44 there are arranged one or more openings 18 in the vicinity of the sealing part 10, so that cavity 13 communicates with cavity 14. Pistons 43 and 44 will, in other words, act as a telescope. This provides the retriever with a long piston travel, even though it is not actually long.

FIG. 4 illustrates a rather well known nipple 25 for application with the present invention. The nipple is fastened to the pipe or tank 34. The nipple 25 has a cylindrical hole 35 which contains the probe 31. Both the hole 35 in the nipple as well as the probe 31 with plug are scaled down or tapered so that the outer part has a larger diameter than the inner part. Upon insertion, the probe 31 will thereby stop against a conic narrowing, which is also used as a sealing surface. The probe 31 is fastened by four set screws or pins 27, which are placed around the circumference at a 90° angle to each other. The pins 27 are provided with threads, and may be screwed into tracks in the probe, or more correctly into the fastener plug part which belongs to it. The probe is thereby held in position.

FIG. 5 illlustrates a ball valve 24, intended to be used in connection with the present invention. It is of a fairly well known type, with a valve body 26 in the shape of a ball, with a passing cylindrical opening. The valve body, or ball 26 may be turned between closed and open position with the help of an outer handle 23.

In the following, the application of the double-acting cylinder will be explained, with reference to FIGS. 6–8. For replacing the probe 31, the operation begins by screwing off the cap 30 of the nipple, and the ball valve 24 is mounted onto the nipple 25. The ball valve 24 is turned to the open position. Then, the hydraulic retriever 1' is mounted to the upper part of the ball valve 24. The hydraulic attachments 19 and 21 are attached to a double-acting pump, e.g. a hand pump which may be adjusted from a first position where hydraulic fluid flows from one attachment to another attachment, and another position which is reversed. The pump is put into the first position, so that the hydraulic fluid flows through in the attachment 19 and out through the attachment 21. Cylinder 2" is then filled with oil, and the pump is operated until the pressure is identical with or somewhat higher than the pressure within the process pipe 34. The situation which is illustrated in FIG. 6 has now been achieved.

Now, the probe 31 is relieved of the pressure in the pipe or tank 34, and the locking pins 27 may be withdrawn to the point where they are no longer in engagement with the groove in the plug. Then, the pump is adjusted to its second position, and upon operating the pump the pistons 43 and 44 will now be withdrawn back into the cylinder 2". If there is sufficient excess pressure in the pipe or tank 34, the probe 31 will be pushed out by the effect of this pressure. If, on the other hand, there is low pressure in the pipe or tank 34, or the probe 31 is stuck in one position or another, the tractive force of the pistons 43 and 44 will pull our the probe 31. We now have the situation which is illustrated in FIGS. 7 and 8. After the probe 31 has passed the ball valve 24, the handle 23 is turned, and the ball valve 24 closed. When the ball valve 24 is closed, the retriever 1' is released from the ball valve 24 with the probe 31, whereupon the probe may be inspected, or replaced by a new probe before it is inserted back into the pipe or tank 34.

Insertion of probe 31 is accomplished by means of the reversal of the process described above. The retriever 1' with probe 31 is screwed onto the ball valve 24. By opening the ball valve 24, the cylinder chamber in front of the probe is filled with fluid. The pump is set in its first position, and the hydraulic fluid is pumped back into the cavity 9. In this way probe 31 is pumped into position. When the probe 31 comes into position in the nipple 25, the locking pins 27 are screwed into place, locking the probe 31 into position.

The retriever 1' and the ball valve 24 are then removed, and as extra security and as a relief measure for locking pins 27, a cap 30 is screwed on. In this way the nipple 25 is back in the same position as originally shown in FIG. 4.

The double-acting hydraulic retriever 1' according to present invention has several advantages. It is constructed with emphasis especially on small size and light weight. This makes it more secure and simpler to operate, and makes it possible also to monitor the pipe or tank in places where it would otherwise be impossible to have access because of the size of traditional mechanical extracting tools. If this tool is applied to pressurized systems of more than 5 bars, the pressure in the pipe or tank 34 may be used for pushing the probe out of the pipe or tank and into the retriever.

It is claimed:

1. A retrieving device for the assembly and disassembly of probes in process pipes, tanks, etc., comprising a nipple mounted to a wall of the pipe or tank, a ball valve mounted to the nipple and a hydraulically activated cylinder which is operated by using a pump after the cylinder is mounted to the ball valve, said cylinder which has an internal cylinder wall is provided with a piston means attached to the pump through a first attachment for the inflow and outflow of hydraulic fluid to said cylinder for balancing the pressure of the piston means within the cylinder so that the probe may be inserted into or out of the nipple through the ball valve and into the retrieving device, said piston means includes a piston rod, said device is characterized in that the piston means further includes a first piston which is slidably and telescopically mounted within a second piston and a first cavity is created between the first piston and the second piston, a second cavity is formed between the second piston and the wall of the cylinder, said first and second pistons are hydraulically connected through an opening therebetween, whereby the cylinder can have a relatively short length while the total combined distance traveled by the first and second pistons and the attached piston rod is sufficient to insert and withdraw the probe from within the process pipe or tank.

2. Device in accordance with claim 1, characterized in that the cylinder wall is scaled down by a shoulder with an inner diameter which is smaller than the outer diameter of the second piston.

3. A retrieving device as defined in claim 1 wherein the cylinder further includes a second attachment for outflow and inflow of hydraulic fluid to said cylinder in the second cavity to telescopically retract said pistons with respect to each other and within said cylinder for assistance in withdrawing said probe from within the process pipe or tank.

4. A retrieving device as defined in claim 1 wherein the piston rod includes means for removably attaching a probe to an end of the piston rod.

5. Device in accordance with claim 4, characterized in that the piston rod attachment means is provided with threads which correspond to threads on the attachment.

* * * * *